(12) United States Patent
Lu et al.

(10) Patent No.: US 10,517,975 B2
(45) Date of Patent: Dec. 31, 2019

(54) LIGHT SOURCE APPARATUS AND METHOD OF USING THE SAME

(71) Applicant: Industrial Technology Research Institute, Hsinchu (TW)

(72) Inventors: Chien-Chun Lu, New Taipei (TW); Chen-Peng Hsu, Hsinchu (TW); Yi-Keng Fu, Hsinchu County (TW); Chia-Fen Hsieh, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 15/826,690

(22) Filed: Nov. 30, 2017

(65) Prior Publication Data

US 2018/0193499 A1 Jul. 12, 2018

Related U.S. Application Data

(60) Provisional application No. 62/445,701, filed on Jan. 12, 2017.

(30) Foreign Application Priority Data

Jul. 21, 2017 (TW) .............................. 106124497 A (51) Int. Cl.
*A61L 2/10* (2006.01)
*A61L 2/24* (2006.01)

(52) U.S. Cl.
CPC ................... *A61L 2/10* (2013.01); *A61L 2/24* (2013.01); *A61L 2202/14* (2013.01)

(58) Field of Classification Search
CPC ..... A61L 2/10; A61L 2/24; A61L 9/20; A61L 9/205
See application file for complete search history.

(56) References Cited

U.S. PATENT DOCUMENTS 5,406,287 A * 4/1995 Pinkus ...................... F41J 2/02
250/495.1
6,656,424 B1 12/2003 Deal
(Continued)

FOREIGN PATENT DOCUMENTS

CN 101681963 3/2010
CN 102667333 9/2012
(Continued)

OTHER PUBLICATIONS

Chien-Chun Lu, et al., "The Efficiency and Reliability Improvement by Utilizing Quartz Airtight Packaging of UVC LEDs," IEEE Transactions on Electron Devices, Jun. 28, 2016, pp. 1-4.
(Continued)

*Primary Examiner* — Eliza W Osenbaugh-Stewart
(74) *Attorney, Agent, or Firm* — JCIPRNET (57) ABSTRACT

A light source apparatus comprises a main body, a plurality of light source modules and a processor. The main body includes a plurality of configuration areas distributed on a surface of the main body. The plurality of configuration areas is oriented towards different directions, respectively. The plurality of light source modules is located in the plurality of configuration areas, respectively. Each of the plurality of light source modules includes a circuit substrate and an ultraviolet emitting device. The processor is electrically connected to the plurality of light source modules. The processor is adapted to drive the ultraviolet emitting device of each of the plurality of light source modules. A method of using a light source apparatus is also provided.

24 Claims, 9 Drawing Sheets

(56) References Cited

U.S. PATENT DOCUMENTS

| | | | |
|---|---|---|---|
| 7,842,932 B2 | 11/2010 | Knight et al. | |
| 8,226,887 B2 | 7/2012 | Harmon et al. | |
| 8,816,301 B2 | 8/2014 | Stibich et al. | |
| 8,993,988 B2 | 3/2015 | Nathan et al. | |
| 9,358,313 B2 | 6/2016 | Deal | |
| 2008/0232115 A1* | 9/2008 | Tsai | F21S 9/03 |
| | | | 362/362 |
| 2011/0089347 A1 | 4/2011 | Knight et al. | |
| 2011/0215261 A1* | 9/2011 | Lyslo | A61L 2/10 |
| | | | 250/492.1 |
| 2012/0062151 A1* | 3/2012 | Lin | F21V 19/0035 |
| | | | 315/312 |
| 2012/0228524 A1* | 9/2012 | Matui | B01J 19/123 |
| | | | 250/494.1 |
| 2014/0158917 A1 | 6/2014 | Stibich et al. | |
| 2014/0292192 A1* | 10/2014 | Rodinger | H05B 33/0806 |
| | | | 315/32 |
| 2015/0102235 A1* | 4/2015 | Lee | A61L 2/10 |
| | | | 250/492.1 |
| 2015/0211706 A1* | 7/2015 | Su | F21V 3/02 |
| | | | 362/157 |
| 2016/0020371 A1* | 1/2016 | Kang | H01L 33/60 |
| | | | 257/91 |
| 2016/0114067 A1* | 4/2016 | Dobrinsky | A61L 2/10 |
| | | | 250/461.1 |
| 2016/0136312 A1* | 5/2016 | Park | F21V 23/003 |
| | | | 362/231 |
| 2016/0151521 A1 | 6/2016 | Nathan et al. | |

FOREIGN PATENT DOCUMENTS

| | | |
|---|---|---|
| TW | M488747 | 10/2014 |
| TW | M524715 | 7/2016 |
| TW | I561760 | 12/2016 |

OTHER PUBLICATIONS

Ji Yeon Lee, "Tuberculosis Infection Control in Health-Care Facilities: Environmental Control and Personal Protection," Tuberculosis and Respiratory Diseases, vol. 79, No. 4, Oct. 2016, pp. 234-240.

Nicholas G. Reed, "The History of Ultraviolet Germicidal Irradiation for Air Disinfection," Public Health Reports, vol. 125, Jan.-Feb. 2010, pp. 15-27.

* cited by examiner

LIGHT SOURCE APPARATUS AND METHOD OF USING THE SAME

CROSS-REFERENCE TO RELATED APPLICATION

This application claims the priority benefits of U.S. provisional application Ser. No. 62/445,701, filed on Jan. 12, 2017 and Taiwan application serial no. 106124497, filed on Jul. 21, 2017. The entirety of each of the above-mentioned patent applications is hereby incorporated by reference herein.

TECHNICAL FIELD

The technical field relates to a light source apparatus and a method of using the same.

BACKGROUND

With the enhancement of the luminous efficiency and the increase of the luminous band of ultraviolet light emitting diode (UVC-LED), the demand for a variety of applications is also increasing. For example, water sterilization, gas sterilization, food sterilization, medical equipment and the like may be applied. The wavelength of the ultraviolet-C (UV-C) is 200 nm to 280 nm and high energy. The UV-C can penetrate the film of virus, bacteria, fungi and dust, attack deoxyribonucleic acid (DNA) and annihilate these harmful organisms.

The current used deep ultraviolet light is low luminous density per unit, bulky, poor directivity, and high driving voltage (110V-220V). And the deep ultraviolet light containing mercury is harmful to the environment. The light source of UVC-LED has characteristics of small size, good directivity, low driving voltage and environmental protection. Therefore, how to design a sterile light source equipment that is easy to use and do not need special construction and can be installed, is one of the important goals of the skill person in the art to be committed to achieving.

SUMMARY

An exemplary embodiment of the disclosure relates to a light source apparatus. The light source apparatus includes a main body, a plurality of light source modules and a processor. The main body includes a plurality of configuration areas. The plurality of configuration areas are distributed on a surface of the main body and oriented towards different directions, respectively. The plurality of light source modules is located in the plurality of configuration areas, respectively. Each of the plurality of light source modules includes a circuit substrate and an ultraviolet emitting device. The ultraviolet emitting device is located on the circuit substrate and is adapted to provide an ultraviolet source. The processor is electrically connected to the plurality of light source modules. The processor is adapted to drive the ultraviolet emitting device of the each of the plurality of light source modules.

An exemplary embodiment of the disclosure relates to a method of using a light source apparatus. The method of using the light source apparatus includes: starting the processor of the light source apparatus described above, wherein the processor drives the ultraviolet emitting device of each of the plurality of light source modules of the light source apparatus; and providing the ultraviolet source by the ultraviolet emitting device of the each of the plurality of light source modules.

The foregoing will become better understood from a careful reading of a detailed description provided herein below with appropriate reference to the accompanying drawings.

DESCRIPTION OF THE EMBODIMENTS

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

Figure 1:
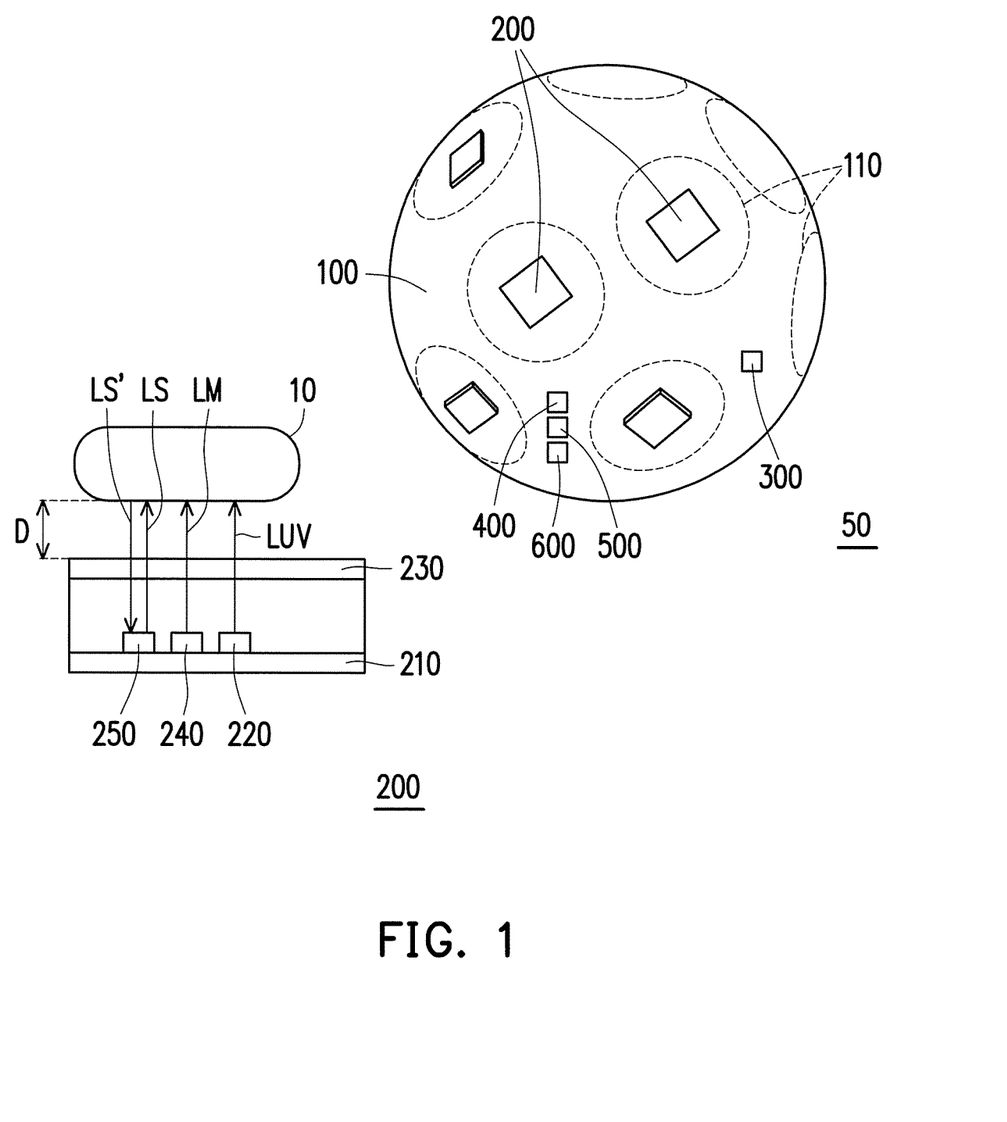
FIG. 1 is a schematic diagram of a light source apparatus and a light source module according to an embodiment of this disclosure.

FIG. 1 is a schematic diagram of a light source apparatus and a light source module according to an embodiment of this disclosure. Referring to FIG. 1, in this embodiment, a light source apparatus 50 comprises a main body 100, a plurality of light source modules 200 and a processor 300. The main body 100 includes a plurality of configuration areas 110, the plurality of configuration areas 110 are distributed on a surface of the main body 100 and are respectively oriented towards different directions. In this embodiment, the shape of the main body 100 is a sphere. However, the scope of the disclosure is not limited thereto. The main body 100 may be made of metal, such as aluminum (Al) or other metals, so as to improve the heat dissipation effect of the light source apparatus 50. The plurality of light source modules 200 are respectively located in the plurality of configuration areas 110, that is, each of the plurality of configuration areas 110 corresponds to one of the plurality of light source modules 200 therein. Each of the plurality of light source modules 200 comprises a circuit substrate 210 and an ultraviolet emitting device 220, and the ultraviolet emitting device 220 is located on the circuit substrate 210 and adapted to provide an ultraviolet source LUV. The ultraviolet emitting device 220 is, for example, an ultraviolet light emitting diode. However, the scope of the disclosure is not limited thereto. Since the ultraviolet source LUV emitted by each of the plurality of light source modules 200 is approximately perpendicular to one of the plurality of configuration areas 110 corresponding to the each of the plurality of light source modules 200. Therefore, the ultraviolet source LUV provided by the light source apparatus 50 is emitted from the surface of the main body 100 outwardly and towards the different directions respectively. The ultraviolet source LUV of the light source apparatus 50 is an omnidirectional light (360 degrees) for sterilization and disinfection. The processor 300 is electrically connected to the plurality of light source modules 200, and the processor 300 is adapted to drive the ultraviolet emitting device 220 of each of the plurality of light source modules 200. Moreover, in other embodiments, the processor 300 may also individually drive the plurality of light source modules 200 such that the light source apparatus 50 is partially illuminated to provide a portion of the luminous angle.

The ultraviolet source LUV provided by the ultraviolet emitting device 220 of each of the plurality of light source modules 200 is, for example, medium-wave ultraviolet (ultraviolet B (UVB) with a wavelength ranging from 280 nm to 315 nm), short-wave ultraviolet (ultraviolet C (UV C) with a wavelength ranging from 100 nm to 280 nm) and so on. Specifically, the short-wave ultraviolet with the wavelength ranging from 200 nm to 280 nm can penetrate the film of viruses, bacteria, fungi and dust, therefore, it can be used as sterilization, disinfection and other purposes.

In one of exemplary embodiments of this disclosure, at least one of the plurality of light source modules 200 further comprises a transparent plate 230. The transparent plate 230 is located on the ultraviolet emitting device 220 so as to protect the ultraviolet emitting device 220. The material of the transparent plate 230 is, for example, quartz glass or other transparent materials. However, the scope of the disclosure is not limited thereto.

In one of exemplary embodiments of this disclosure, at least one of the plurality of light source modules 200 further comprises a visible light emitting device 240 adapted to provide a visible light LM. The visible light emitting device 240 is located on the circuit substrate 210. The visible light emitting device 240 and the ultraviolet emitting device 220 are disposed on the same plane or stacked. The visible light emitting device 240 is, for example, a visible light emitting diode. However, the scope of the disclosure is not limited thereto. An area irradiated by the visible light LM and an area irradiated by the ultraviolet source LUV are at least partially overlapped. In this way, the user knows the area irradiated by the ultraviolet source LUV through the visible light LM. In other words, the user adjusts the light source apparatus 50 to an appropriate position according to the visible light LM, and then the ultraviolet emitting device 220 of the light source apparatus 50 is driven to provide the ultraviolet source LUV for sterilization, sterilization and so on.

In one of exemplary embodiments of this disclosure, at least one of the plurality of light source modules 200 further comprises a distance sensing device 250. The distance sensing device 250 is located on the circuit substrate 210, and both the distance sensing device 250 and the ultraviolet emitting device 220 are disposed on the same plane. The distance sensing device 250 is adapted to sense a distance D from the each of the plurality of light source modules 200 to a front irradiation area 10. The distance sensing device 250 is, for example, an infrared distance sensor. However, the scope of the disclosure is not limited thereto. In one of exemplary embodiments of this disclosure, the distance sensing device 250 emits a sensing ray LS to the front irradiation area 10, and then the sensing ray LS reflects a reflecting ray LS' back to the distance sensing device 250 after the sensing ray LS reaches the front irradiation area 10. The distance sensing device 250 can sense a ray intensity of the reflecting ray LS' and generate a sensing current according to the ray intensity of the reflecting ray LS'. So that the distance D from the each of the plurality of light source modules 200 to the front irradiation area 10 can be calculated.

In one of exemplary embodiments of this disclosure, the processor 300 is electrically connected to the distance sensing device 250. The processor 300 adjusts a luminous intensity of the ultraviolet emitting device 220 according to the distance D sensed by the distance sensing device 250. Specifically, the processor 300 provides a corresponding driving current through the circuit substrate 210 according to the distance D, so as to drive the ultraviolet emitting device 220 and adjust the luminous intensity of the ultraviolet emitting device 220. In other words, the processor 300 reduces the corresponding driving current when the value of the distance D is less. The processor 300 increases the corresponding driving current when the value of the distance D is greater. Therefore, the light source apparatus 50 may improve the effect of sterilization and disinfection and use energy effectively.

For example, in the light source apparatus 50, a distance from one of the plurality of light source modules 200 to its respective front irradiation area 10 is a distance D, wherein the distance D is not equal to a distance from another one of the plurality of light source modules 200 to its respective front irradiation area 10. Also, a luminous intensity of said one of the plurality of light source modules 200 is different from a luminous intensity of said another one of the plurality of light source modules 200. In other words, the light source apparatus 50 can simultaneously emit different directions and different intensities of the ultraviolet source LUV. That is, each of the plurality of light source modules 200 can independently emit an appropriate intensity of the ultraviolet source LUV.

In one of exemplary embodiments of this disclosure, the light source apparatus 50 further comprises a motion detector 400. The motion detector 400 is located on the main body 100 and adapted to detect whether a biological body is in a sterilizing space or not. Once the motion detector 400 detects that there is a biological body in the sterilization space when the light source apparatus 50 is in operation, the light source apparatus 50 stops the operation, so as to avoid the damage of the ultraviolet source LUV to the biological body, and improve the safety when the light source apparatus 50 is in use. The detection method of the motion detector 400 may be, for example, sensing the displacement, the heat source or the image. However, the scope of the disclosure is not limited thereto.

In one of exemplary embodiments of this disclosure, the light source apparatus 50 further comprises a warning device 500. The warning device 500 is located on the main body 100 and adapted to emit a warning signal. The warning device 500 emits the warning signal when the light source apparatus 50 is in operation, to warn the biological body not to enter the sterilization space for reducing the damage of the ultraviolet source LUV to the biological body, and to improve the safety when the light source apparatus 50 is in use. The warning device 500 may be, for example, a warning light or a warning sound. However, the scope of the disclosure is not limited thereto.

In one of exemplary embodiments of this disclosure, the light source apparatus 50 further comprises a transceiver module 600 so that the light source apparatus 50 has a mutual detection function. Specifically, the transceiver module 600 is located on the main body 100 and includes a transmitting unit and a receiving unit. The transmitting unit transmits a signal such as a wireless signal. The receiving unit receives a signal from another light source apparatus 50. The relative position and the distance between the two light source apparatuses 50 can be judged through the strength of the received signal. Thus whether the two light source apparatuses 50 are interconnected to form a sterilization region or not is detectable. Therefore, the light source apparatus 50 has a mutual detection function.

Figure 2:
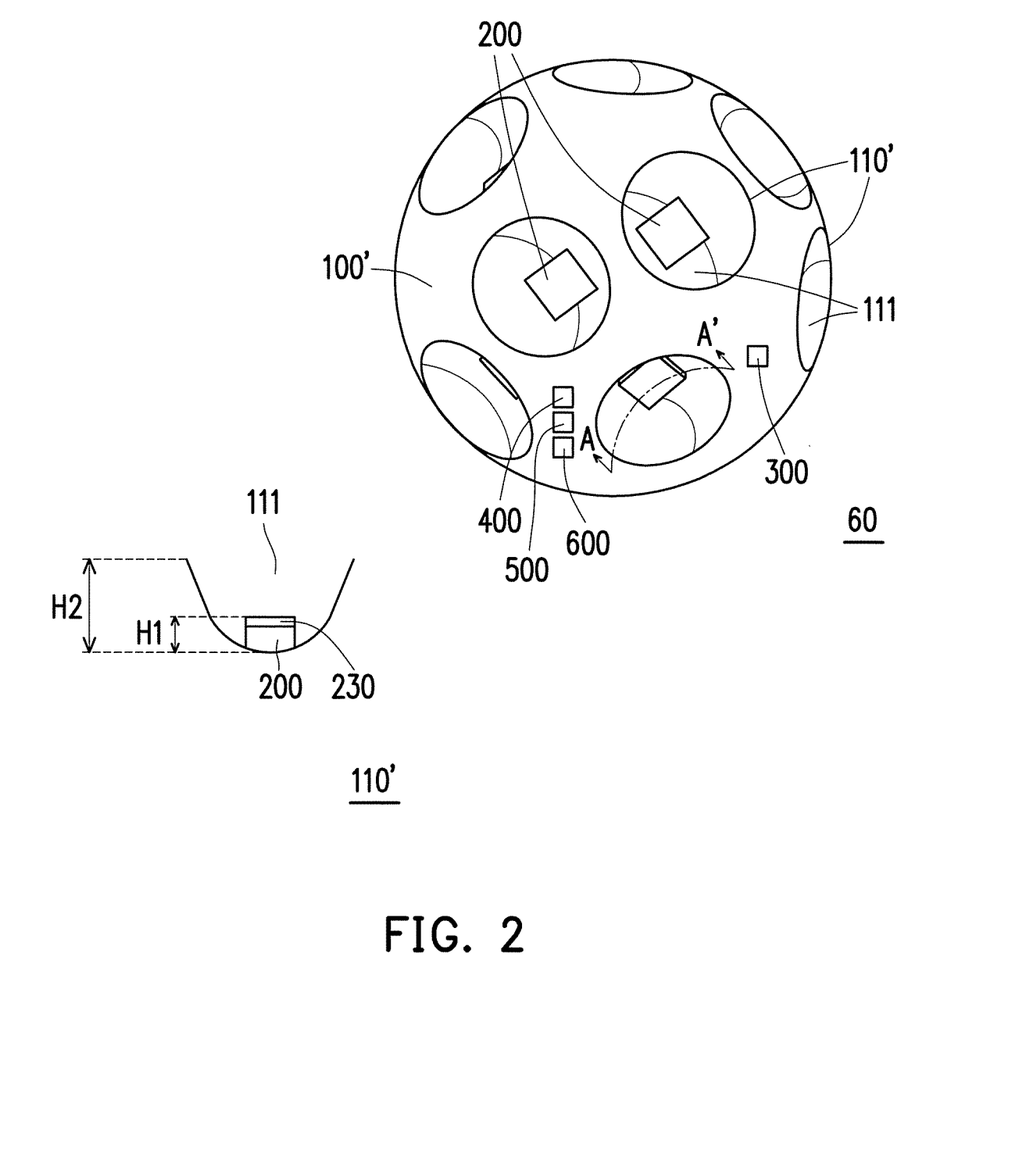
FIG. 2 is a schematic diagram of a light source apparatus according to another embodiment of this disclosure.

FIG. 2 is a schematic diagram of a light source apparatus according to another embodiment of this disclosure. The embodiment of FIG. 2 is similar to the embodiment of FIG. 1. Like reference numerals refer to like elements, and the same description will not be repeated herein. The difference between the two embodiments is the plurality of configuration areas of the main body.

Referring to the embodiment in FIG. 2, a light source apparatus 60 comprises a main body 100', a plurality of light source modules 200 and a processor 300. The main body 100' includes a plurality of configuration areas 110'. The plurality of configuration areas 110' are recessed inwardly from the surface of the main body 100' to form a plurality of accommodating recesses 111, respectively. The plurality of light source modules 200 are respectively embedded in the bottom of the plurality of accommodating recesses 111 of the plurality of configuration areas 110'. Referring to the embodiment in FIG. 2, a schematic cross-sectional view along a line AA' in one configuration area 110'. The top surface of the transparent plate 230 of the light source module 200 is located at a first horizontal height H1. The top of the opening of the accommodating recesses 111 is located at a second horizontal height H2. The second horizontal height H2 is higher than the first horizontal height H1. For example, the second horizontal height H2 is 2.5 times higher than the first horizontal height H1, that is H2>2.5H1. In this way, it prevents the transparent plate 230 from cracking due to being directly touched.

In one of exemplary embodiments of this disclosure, an inner wall of each of the plurality of accommodating recesses 111 includes a photocatalyst layer (not shown). The photocatalyst layer can accelerate the catalysis of photochemical reactions. The photocatalyst layer may be made of gallium phosphide (GaP), gallium arsenide (GaAs), titanium dioxide (TiO$_2$) or any suitable photocatalyst. In one of exemplary embodiments of this disclosure, an inner wall of each of the plurality of accommodating recesses 111 includes a reflective layer (not shown). The ultraviolet source LUV emitted in the inner wall of the accommodating recesses 111 is reflected by the reflective layer and sent to the outside of the opening of the accommodating recesses 111 for reducing the loss of the ultraviolet source LUV, thereby increasing the use efficiency of the light source apparatus 60. In this embodiment, the shape of the accommodating recesses 111 is a bowl shape. However, the scope of the disclosure is not limited thereto.

Figure 3:
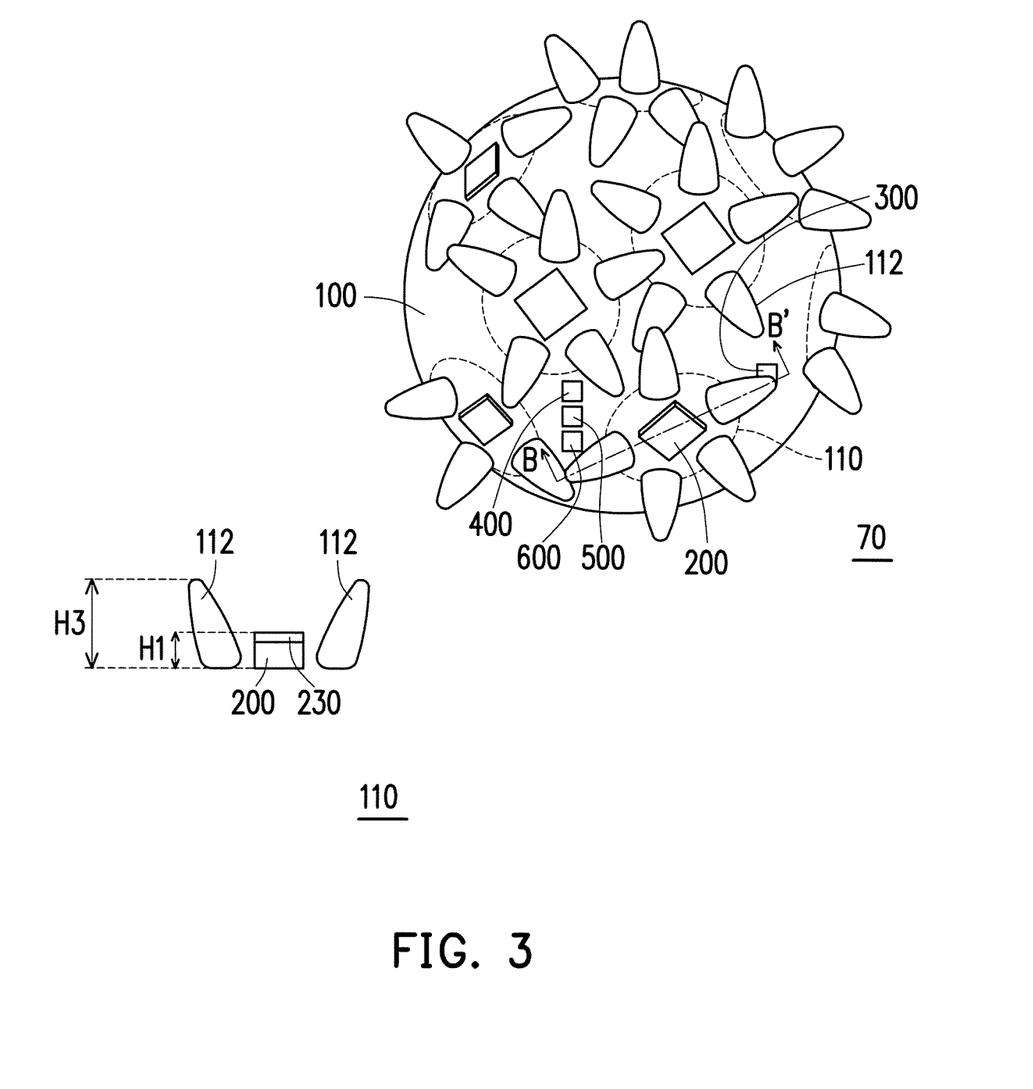
FIG. 3 is a schematic diagram of a light source apparatus according to an alternative embodiment of this disclosure.

FIG. 3 is a schematic diagram of a light source apparatus according to an alternative embodiment of this disclosure. The embodiment of FIG. 3 is similar to the embodiment of FIG. 1. Like reference numerals refer to like elements, and the same description will not be repeated herein. The difference between the two embodiments is at least one convex structure 112 is included in the embodiment of FIG. 3.

Referring to the embodiment of FIG. 3, a light source apparatus 70 comprises the main body 100, the plurality of light source modules 200 and the processor 300. The main body 100 includes the plurality of configuration areas 110. The light source apparatus 70 further comprises at least one convex structure 112. The at least one convex structure 112 surrounds the plurality of light source modules 200 and is located on the main body 100 and protrudes outwardly from the surface of the main body 100. The light source apparatus 70 is shaped like a hedgehog. However, the scope of the disclosure is not limited thereto. Referring to FIG. 3, a schematic cross-sectional view along a line BB' in one configuration area 110. The top surface of the transparent plate 230 of the light source module 200 is located at the first horizontal height H1. The top of the convex structure 112 is located at a third horizontal height H3. The third horizontal height H3 is higher than the first horizontal height H1. For example, the third horizontal height H3 is 2.5 times higher than the first horizontal height H1, that is H3>2.5H1. In this way, it prevents the transparent plate 230 from cracking due to being directly touched.

In one of exemplary embodiments of this disclosure, a surface of each of the convex structure 112 includes a photocatalyst layer (not shown). The Photocatalyst layer can accelerate the catalysis of photochemical reactions. The photocatalyst layer may be gallium phosphide (GaP), gallium arsenide (GaAs), titanium dioxide (TiO$_2$) or any suitable photocatalyst. In one of exemplary embodiments of this disclosure, a surface of each of the convex structure 112 includes a reflective layer (not shown). The ultraviolet source LUV emitted on the surface of the convex structure 112 is reflected by the reflective layer and sent to outside the convex structure 112 for reducing the loss of the ultraviolet source LUV, thereby increasing the use efficiency of the light source apparatus 70. In this embodiment, the shape of the convex structure 112 is a strip shape. However, the scope of the disclosure is not limited thereto.

Figure 4A:
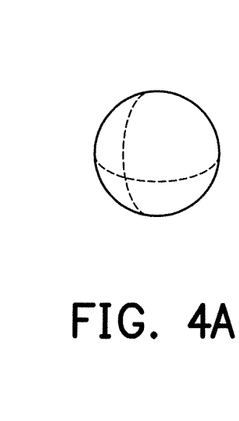
FIGS. 4A-4H are schematic diagrams of a variety of shapes of the main body of a light source apparatus, respectively, according to embodiments of this disclosure.
Figure 4B:
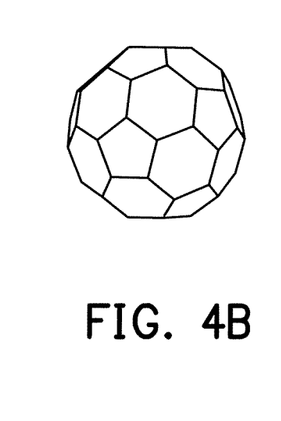
Figure 4C:
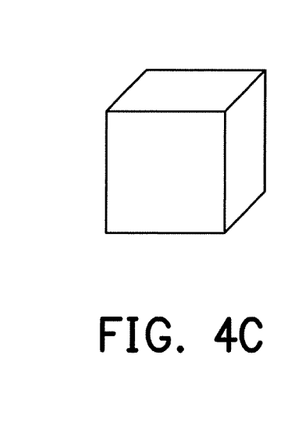
Figure 4D:
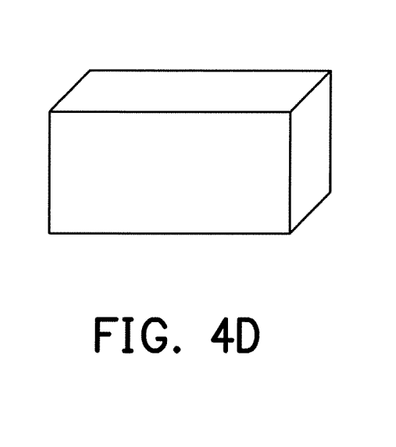
Figure 4E:
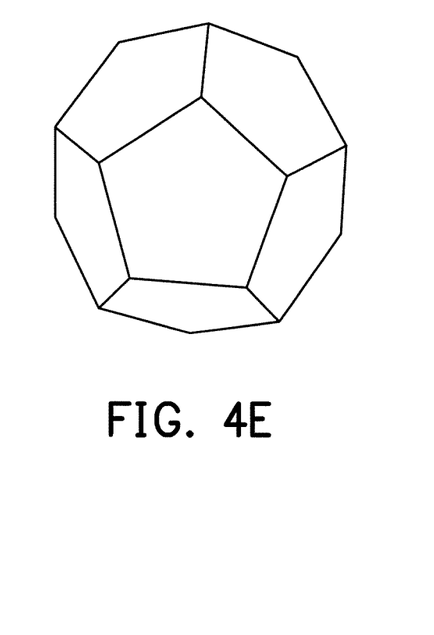
Figure 4F:
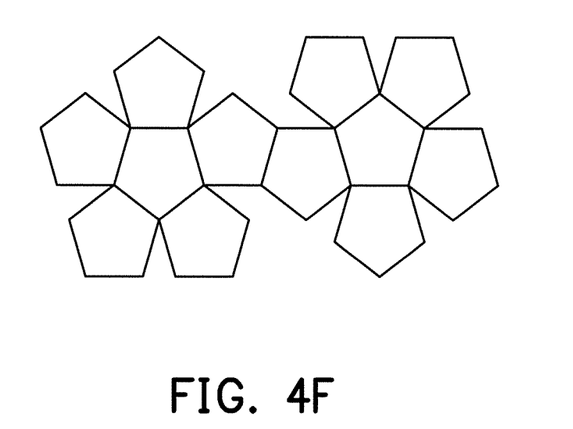
Figure 4G:
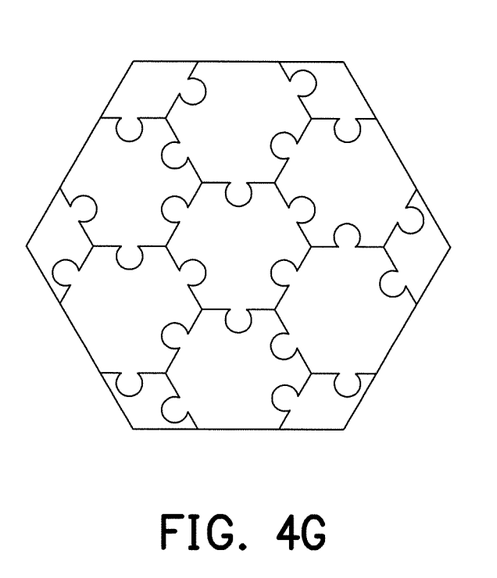
Figure 4H:
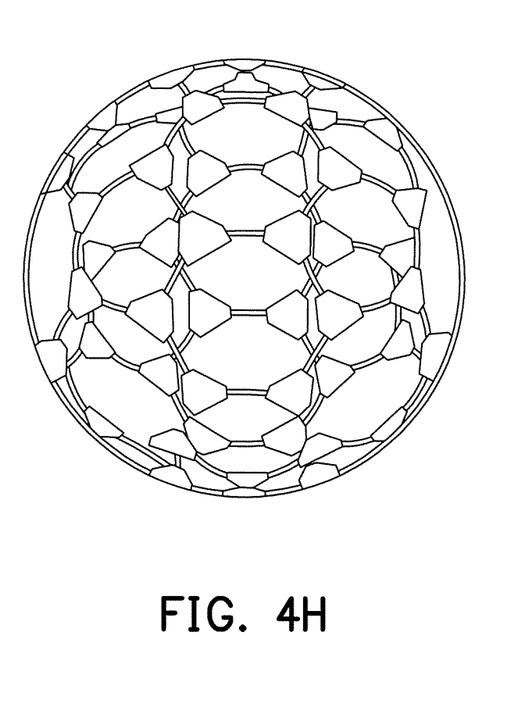

FIGS. 4A-4H are schematic diagrams of a variety of shapes of the main body of a light source apparatus, respectively, according to embodiments of this disclosure. Referring to FIG. 4A, the shape of the main body of the above-mentioned light source apparatus 50, 60 or 70 is a sphere. However, the scope of the disclosure is not limited thereto. In other embodiments, the shape of the main body of the light source apparatus 50, 60 or 70 may be a polyhedron. For example, the embodiment shown in FIG. 4B is a geometric form consisting of pentagons, hexagons and straight edges in a 3-dimensional space. The embodiment shown in FIG. 4C is a cube. The embodiment shown in FIG. 4D is a cuboid. The embodiment shown in FIG. 4E is a dodecahedron. The embodiment shown in FIG. 4F is a dodecahedron expanded view. Wherein the expanded view of FIG. 4E is shown in FIG. 4F. And the light source apparatus of FIG. 4F may be applied to flat sterilization. The embodiment shown in FIG. 4G is a combination of multiple polygons. The shape of the main body may be arranged in any combination. The embodiment shown in FIG. 4H, The main body may be combined by a plurality of connecting members to form a hollow shape, similar to fullerene shape. In summary, the shape of the main body may be designed to meet irregular shapes. The main body of the light source apparatus 50, 60 or 70 may be made of metal, such as aluminum (Al) or other good heat dissipation materials. The heat dissipation effect of the light source apparatus 50, 60 or 70 can be improved. However, the scope of the disclosure is not limited thereto.

Figure 5:
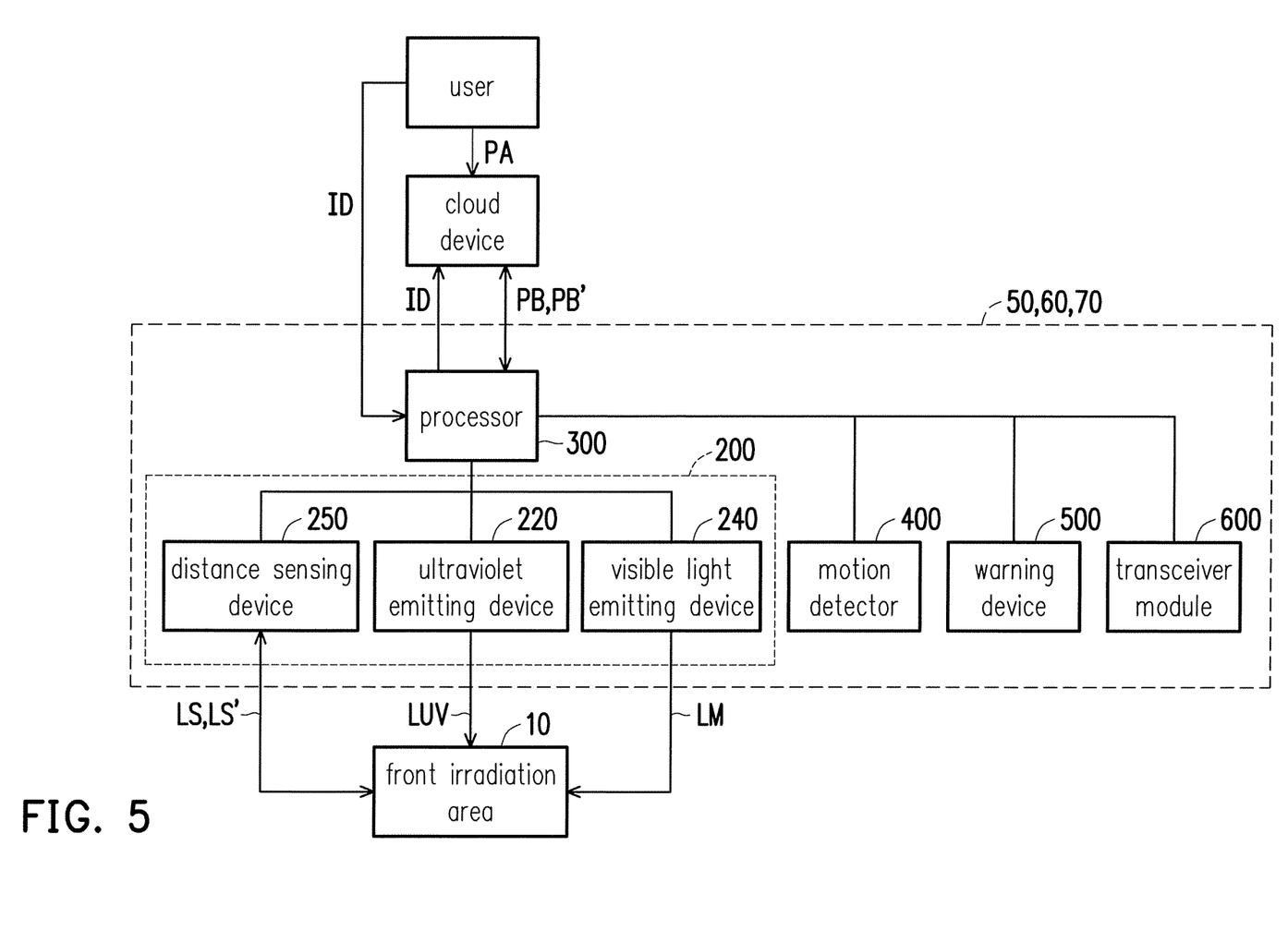
FIG. 5 is a schematic diagram of a method of using a light source apparatus according to an embodiment of this disclosure.

FIG. 5 is a schematic diagram of a method of using a light source apparatus according to an embodiment of this disclosure. The using method according to the present embodiment may be adapted to the light source apparatuses 50, 60 and 70 shown in FIG. 1, FIG. 2 and FIG. 3, respectively. In one of exemplary embodiments of this disclosure, the method of using the light source apparatus (such as the light source apparatus 50, 60 or 70) includes the following steps. A visible light emitting device 240 of the light source apparatus is started for providing a visible light LM. The user knows the area irradiated by the light source apparatus through the visible light LM. The user adjusts the light source apparatus to an appropriate position according to the visible light LM and confirms that the area irradiated is correct. Then, the processor 300 is started to drive the ultraviolet emitting device 220 to provide the ultraviolet source LUV for the irradiated area. In this way, it prevents the ultraviolet source LUV from irradiating to the non-irradiated area and generating damages, thereby improving the safety when the light source apparatus is in use.

In one of exemplary embodiments of this disclosure, a method of starting the light source apparatus (such as the light source apparatus 50, 60 or 70) includes the following steps. The distance sensing device 250 is started to sense a distance D from a light source module 200 to a front irradiation area 10. The ultraviolet emitting device 220 of the light source module 200 is driven by the processor 300 according to the distance D to provide the ultraviolet source LUV. A luminous intensity of the ultraviolet emitting device 220 is adjusted by the processor 300 according to the distance D. In this way, the use efficiency of the light source module 200 is increased. That is, the use efficiency and the safety of the light source apparatus are increased.

In another exemplary embodiment of this disclosure, a method of starting the light source apparatus (such as the light source apparatus 50, 60 or 70) includes the following. The light source apparatus is started according to an identification data ID. In other words, the user may confirm whether a use object of the light source apparatus is correct or not according to a corresponding identification data ID. After confirming the use object of the light source apparatus is correct, the light source apparatus is started. So that, the light source apparatus further provides an appropriate confirmation and protection mechanism for the user.

In yet another exemplary embodiment of this disclosure, the method of using the light source apparatus (such as the light source apparatus 50, 60 or 70) includes the following steps. A sterilization parameter PB in a cloud device is downloaded according to an identification data ID of a user. A driving time and a luminous intensity of the ultraviolet emitting device 220 are controlled by the processor 300 according to the sterilization parameter PB. Specifically, the user may provide an instruction parameter PA to the cloud device according to the space environment situation and store as the sterilization parameter PB that can be identified by the light source apparatus, or the user may download the sterilization parameter PB from the cloud device according the identification data ID of the user and modify the sterilization parameter PB. The processor 300 of the light source apparatus adjusts the driving time and the luminous intensity of the ultraviolet emitting device 220 according to the sterilization parameter PB.

In one of exemplary embodiments of this disclosure, the method of using the light source apparatus (such as the light source apparatus 50, 60 or 70) includes the following. The sterilization parameter PB' is uploaded to the cloud device according to the driving condition of the processor 300.

In one of exemplary embodiments of this disclosure, the method of using the light source apparatus (such as the light source apparatus 50, 60 or 70) can be used with an Unmanned Aerial Vehicle (UAV) or a mobile machine. The light source apparatus is positioned on the UAV or the mobile machine and is moved to an appropriate position by the movement of the UAV or the mobile machine.

Figure 6A:
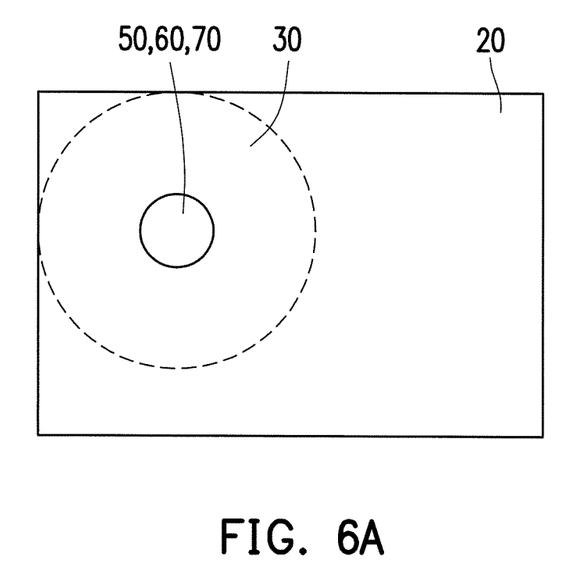
FIGS. 6A-6C are schematic diagrams of a method of using a light source apparatus according to another embodiment of this disclosure.
Figure 6B:
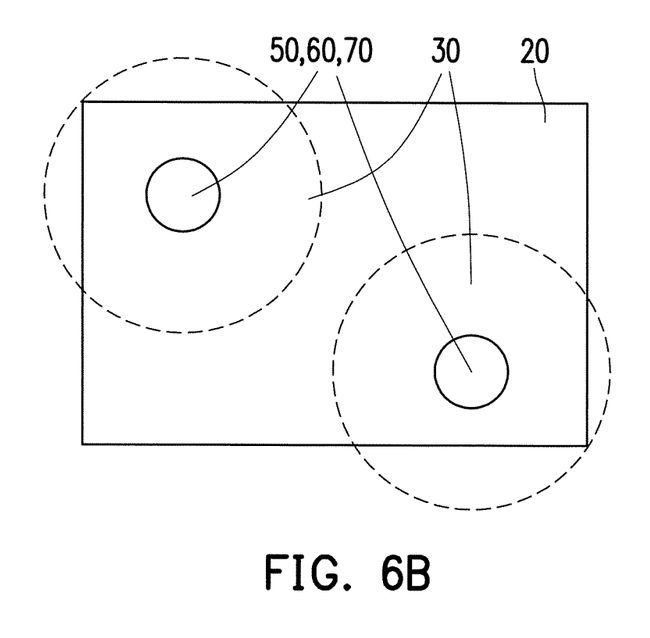
Figure 6C:
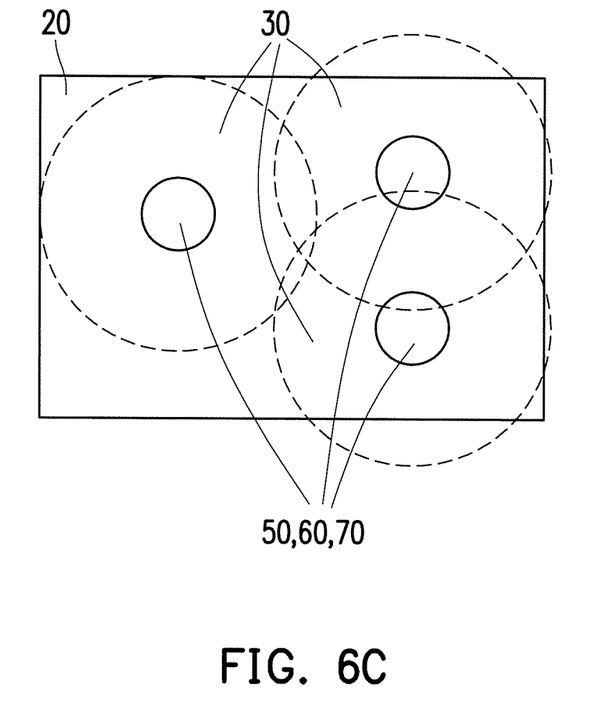

FIGS. 6A-6C are schematic diagrams of a method of using a light source apparatus according to another embodiment of this disclosure. The using method according to the present embodiment may be adapted to the light source apparatuses 50, 60 and 70 shown in FIG. 1, FIG. 2 and FIG. 3, respectively. In one of exemplary embodiments of this disclosure, each of a plurality of light source apparatuses has a mutual detection function by using a transceiver module 600 of the each of the plurality of light source apparatuses, so as to the plurality of light source apparatuses can be interconnected to form a sterilization region. Referring to FIG. 6A, a single light source apparatus 50, 60 or 70 (denoted by 50, 60, 70) is placed above a waiting sterilization surface 20 and provides a unit sterilization area 30. A single light source apparatus 50, 60 or 70 does not receive a signal from another light source apparatus and does not form a sterilization region. Therefore, the single light source apparatus 50, 60 or 70 may issue an indication signal such as a flashing red visible light. A single light source apparatus fails to provide a one-time complete sterilization when the area of the waiting sterilization surface 20 is greater than the area of the unit sterilization area 30.

Referring to FIG. 6B, two light source apparatuses (such as a combination of a group consisting of the light source apparatuses 50, 60 and 70) are respectively placed above two corners of a waiting sterilization surface 20. One light source apparatus receives a weaker signal from another light source apparatus as the distance between the two light source apparatuses is too far. The two light source apparatuses are not interconnected and do not form a sterilization region. That is, the two unit sterilization areas 30 do not overlap. Therefore the two light source apparatuses respectively issue an indication signal such as a flashing red visible light. The user realizes that the two light source apparatuses are not interconnected because the distance between the two light source apparatuses is too far.

Referring to FIG. 6C, three light source apparatuses (such as another combination of a group consisting of the light source apparatuses 50, 60 and 70) are respectively placed above three corners of a waiting sterilization surface 20. One of the three light source apparatuses receives a stronger signal from two other light source apparatuses as the distance between every two of the three light source apparatuses is appropriate. The three light source apparatuses are interconnected to form a sterilization region. That is, the three unit sterilization areas 30 overlap. Therefore each of the three light source apparatuses may independently issue an indication signal such as a flashing green visible light. The user realizes that the three light source apparatuses are interconnected because the distance between every two of the three light source apparatuses is appropriate. Therefore, a single unit sterilization area 30 provided by a single light source apparatus fails to provide a one-time complete sterilization when the area of the waiting sterilization surface 20 is greater. While, with the mutual detection functions of the plurality of light source apparatuses, the unit sterilization areas of the plurality of light source apparatuses are interconnected to form a sterilization region, therefore, a one-time complete sterilization can be performed. This achieves a fast and efficient sterilization effect.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A light source apparatus, comprising:
   a main body including a plurality of configuration areas, wherein the plurality of configuration areas are distributed on a surface of the main body and oriented towards different directions, respectively;
   a plurality of light source modules located in the plurality of configuration areas, respectively, each of the plurality of light source modules comprising:
      a circuit substrate; and
      an ultraviolet emitting device located on the circuit substrate and adapted to provide an ultraviolet source; and
   a processor electrically connected to the plurality of light source modules, wherein the processor is adapted to drive the ultraviolet emitting device of the each of the plurality of light source modules,
   wherein the processor individually drives each of the plurality of light source modules to control a luminous intensity according to a distance of an irradiation area.

2. The light source apparatus as claimed in claim 1, wherein at least one of the plurality of light source modules further comprises a transparent plate located on the ultraviolet emitting device.

3. The light source apparatus as claimed in claim 1, wherein a wavelength of the ultraviolet source ranges from 200 nm to 280 nm.

4. The light source apparatus as claimed in claim 1, wherein the main body is expanded to form a flat.

5. The light source apparatus as claimed in claim 1, wherein at least one of the plurality of light source modules further comprises a visible light emitting device located on the circuit substrate and adapted to provide a visible light, wherein an area irradiated by the visible light and an area irradiated by the ultraviolet source are at least partially overlapped.

6. The light source apparatus as claimed in claim 1, wherein at least one of the plurality of light source modules further comprises a distance sensing device located on the circuit substrate and adapted to sense a distance from the at least one of the plurality of light source modules to a front irradiation area.

7. The light source apparatus as claimed in claim 1, wherein the plurality of configuration areas are recessed inwardly from the surface of the main body to form a plurality of accommodating recesses, respectively.

8. The light source apparatus as claimed in claim 7, wherein an inner wall of each of the plurality of accommodating recesses includes a photocatalyst layer.

9. The light source apparatus as claimed in claim 7, wherein an inner wall of each of the plurality of accommodating recesses includes a reflective layer.

10. The light source apparatus as claimed in claim 1, further comprising at least one convex structure located on the main body and surrounding the plurality of light source modules.

11. The light source apparatus as claimed in claim 10, wherein a surface of each of the at least one convex structure includes a photocatalyst layer.

12. The light source apparatus as claimed in claim 10, wherein a surface of each of the at least one convex structure includes a reflective layer.

13. The light source apparatus as claimed in claim 1, further comprising a motion detector located on the main body and adapted to detect a biological body in a sterilizing space.

14. The light source apparatus as claimed in claim 1, further comprising a warning device located on the main body and adapted to emit a warning signal.

15. The light source apparatus as claimed in claim 1, further comprising a transceiver module located on the main body and adapted to detect whether at least two light source apparatuses are interconnected so as to form a sterilization region through their respective transceiver modules of the at least two light source apparatuses.

16. A method of using a light source apparatus, comprising:
   starting the processor of the light source apparatus as claimed in claim 1, wherein the processor drives the ultraviolet emitting device of each of the plurality of light source modules of the light source apparatus; and
   providing the ultraviolet source by the ultraviolet emitting device of the each of the plurality of light source modules.

17. The method of using the light source apparatus as claimed in claim 16, further comprising:
   starting a visible light emitting device of the light source apparatus to provide a visible light; and
   adjusting the light source apparatus to an appropriate position according to the visible light.

18. The method of using the light source apparatus as claimed in claim 16, wherein a method of starting the light source apparatus comprises:
   starting a distance sensing device of one of the plurality of light source modules to sense a distance from the one of the plurality of light source modules to a front irradiation area;
   driving the one of the plurality of light source modules by the processor according to the distance, from the one of the plurality of light source modules to the front irradiation area, to provide the ultraviolet source; and
   adjusting a luminous intensity of the one of the plurality of light source modules by the processor according to the distance from the one of the plurality of light source modules to the front irradiation area.

19. The method of using the light source apparatus as claimed in claim 16, wherein a method of starting the light source apparatus comprises:
   starting the light source apparatus according to an identification data.

20. The method of using the light source apparatus as claimed in claim 16, further comprising:
   downloading a sterilization parameter in a cloud device according to an identification data; and
   controlling a driving time and a luminous intensity of the each of the plurality of light source modules by the processor according to the sterilization parameter.

21. The method of using the light source apparatus as claimed in claim 16, further comprising:
   positioning the light source apparatus on a mobile machine, and moving the light source apparatus to an appropriate position by the mobile machine.

22. The method of using the light source apparatus as claimed in claim 16, further comprising:
   starting a transceiver module of the light source apparatus;
   issuing an indication signal of the light source apparatus according to the transceiver module; and
   realizing whether at least two light source apparatuses are interconnected to form a sterilization region according to their respective indication signals of the at least two light source apparatuses.

23. The light source apparatus as claimed in claim 1, wherein the main body is a sphere or a polyhedron.

24. The light source apparatus as claimed in claim 1, wherein ultraviolet sources provided by ultraviolet emitting devices of the plurality of light source modules form an omnidirectional light.

\* \* \* \* \*